United States Patent [19]

Arcamone et al.

[11] 4,020,270
[45] Apr. 26, 1977

[54] L-LYXOHEX-1-ENOPYRANOSE DERIVATIVE

[75] Inventors: Federico Arcamone, Milan; Giuseppe Cassinelli, Voghera (Pavia), both of Italy

[73] Assignee: Societa' Farmaceutici Italia S.p.A., Milan, Italy

[22] Filed: Jan. 19, 1976

[21] Appl. No.: 650,519

Related U.S. Application Data

[62] Division of Ser. No. 568,437, April 16, 1975.

[30] Foreign Application Priority Data

May 2, 1974 United Kingdom ............ 19209/74

[52] U.S. Cl. .................. 536/18; 260/396 R; 424/180; 536/4; 536/17
[51] Int. Cl.² ............................... C07H 5/06
[58] Field of Search ......... 260/210 R, 211; 536/18

[56] References Cited
UNITED STATES PATENTS 3,803,124  4/1974  Arcamone et al. ............ 260/210 R

OTHER PUBLICATIONS

Noller "Chem. of Organic Compounds" 3rd Ed. 1965, W. B. Saunders Co., Phila., Pa. pp. 123–126, 166 and 168.

*Primary Examiner*—Johnnie R. Brown
*Attorney, Agent, or Firm*—Hubbell, Cohen, Stiefel & Gross

[57] ABSTRACT

Anthracyclinone glycoside antibiotics including the known antibiotics daunomycin and adriamycin, as well as other, novel glycoside antibiotics of the formula (VIII):

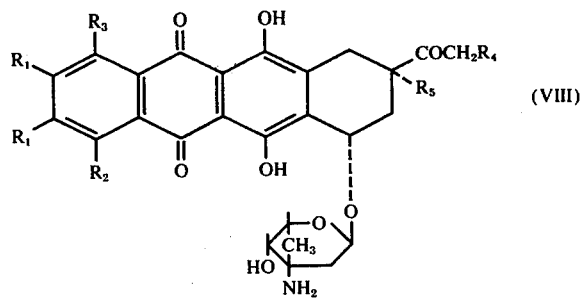

wherein
when $R_1$ is hydrogen, $R_2$ and $R_3$ are each independently hydrogen, methyl, methoxy, chloro, or bromo; and when $R_2$ and $R_3$ are hydrogen, $R_1$ is methyl, chloro, or bromo and $R_4$ and $R_5$ are each independently hydrogen or hydroxy are prepared by an acid catalyzed addition reaction between (a) an anthracyclinone compound of the formula

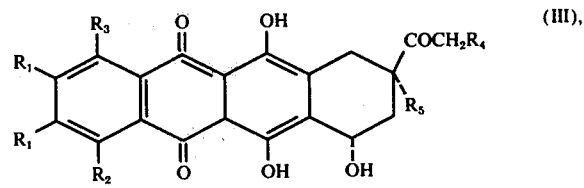

or a dioxolanyl protected derivative thereof (VI) having the formula:

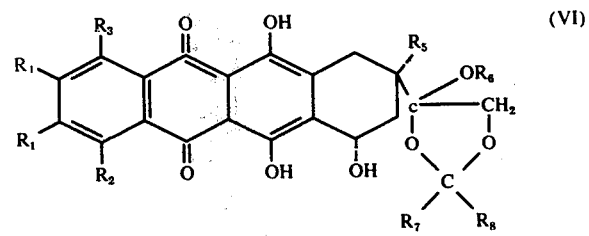

wherein $R_1$, $R_2$, $R_3$, $R_4$ and $R_5$ are as defined above, and $R_6$, $R_7$ and $R_8$ are independently selected from the group consisting of hydrogen and $C_1$–$C_4$ alkyl; or $R_7$ and $R_8$, together with the carbon atom to which they are bound may form a saturated or unsaturated ring of 3–8 carbon atoms and (b) a novel reactive, protected 1,2-unsaturated pyranoid sugar, preferably, 1,2,3,6-tetradeoxy-3-trifluoroacetamido-4-trifluoroacetoxy-L-lyxo-hex-1-enopyranose which forms protected derivatives of said glycoside antibiotics and then removing the protecting groups from said glycoside antibiotics. These antibiotics are useful in the treatment of various human cancers and leukemia such as sarcomas, breast cancer, bronchogenic carcinoma, malignant lymphomas, neuroblastomas, acute leukemia and bladder cancer.

1 Claim, No Drawings

L-LYXOHEX-1-ENOPYRANOSE DERIVATIVE

This is a division of application Ser. No. 568,437 pending, filed Apr. 16, 1975.

CROSS REFERENCE TO RELATED APPLICATIONS

This application is related to and incorporates by reference the contents of copending applications Ser. Nos. 560,104 and 560,105, filed respectively on Mar. 19,1975 and Mar. 19, 1975 and entitled DAUNOMYCINS, PROCESS FOR THEIR PREPARATION AND USES THEREOF AND ADRIAMYCINS, PROCESS FOR THEIR PREPARATION AND USES THEREOF, both applications being in the names of Arcamone, DiMarco and Penco and both being owned by the unrecorded assignee hereof.

BACKGROUND OF THE INVENTION

1. Field of the Invention

The present invention relates to a new process for the preparation of antitumor glycosides including the known antibiotics daunomycin and adriamycin. The process is based on the reaction between protected glycals and anthracyclinones or reactive protected derivatives thereof to produce substituted 2-deoxy-glycosides, which, after removal of the protecting groups are converted to antitumor compounds effective in the treatment of certain forms of human cancer and leukemia, such as sarcomas, breast cancer, bronchogenic carcinoma, malignant lymphomas, neuroblastomas, acute, leukemia and bladder cancer.

2. Prior Art

Glyceside antibiotics are known. For example, daunomycin and its aglycone, daunomycinone are well known compounds. They are described and claimed in British Pat. No. 1,003,383. Adriamycin and its aglycone, adriamycinone are also well known compounds, being described and claimed in British Pat. No., 1,161,278; both such British patents being owned by the unrecorded assignee hereof.

The above glycoside antibiotics are prepared according to the processes disclosed in the Arcamone et al applications incorporated herein by reference by reacting the aglycone, or a reactive derivative thereof with a reactive protected derivative of the pyranose sugars daunosamine and 4'-epidaunosamine.

The present invention utilizes a novel, reactive, protected derivative of a 1,2-unsaturated pyranoid sugar. These compounds are known generically as "glycals". See, for example, the monograph entitled "Unsaturated Sugar, Advances in Carbohydrate Chemistry", Vol. 20, page 67 (1965, Academic Press, London). In this monograph a number of glycals including D-arabinal (3,4-di-O-acetyl); L-arabinal (3,4-di-O-acetyl); D-allal(4,6-O-benzylidene); D-glucal(4-deoxy); L-glucal(3,4-di-O-acetyl), etc., are described.

SUMMARY OF THE INVENTION

The present invention provides, in one aspect thereof, a new process for preparing anthracyclinone glycosides and particularly, daunomycinone and adriamycinone glycosides. More specifically, the invention provides a process, which in preferred embodiments is used for preparing the known glycosides daunomycin and adriamycin.

The process involves the use of a new reactive intermediate glycal which is a further aspect of the invention. Finally, the invention provides a process for preparing this new glycal.

The new reactive intermediate glycal is 1,2,3,6-tetradeoxy-3-trifluoroacetamido-4-trifluoroacetoxy-L-lyxo-hex-1-enopyranose (II). This compound has not heretofore been described in the literature. The present invention provides a novel synthesis for the preparation of this new glycal, which is then utilized as an intermediate for the preparation of the antitumor glycosides in accordance with a further aspect of the invention. Compound (II) has the structure:

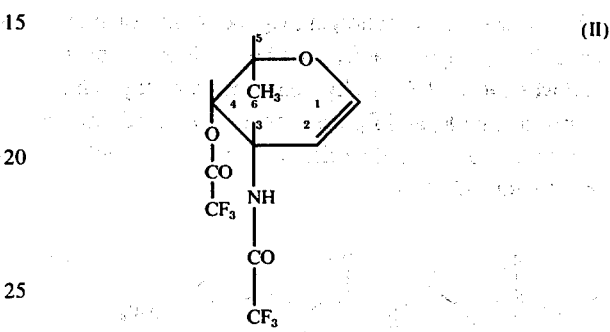

(II)

According to the invention, compound (II) is prepared by reacting 1-chloro-2,3,6-trideoxy-3-trifluoroacetamido-4-trifluoroacetoxy-alpha-L-lyxohexopyranose (I), the structure of which is:

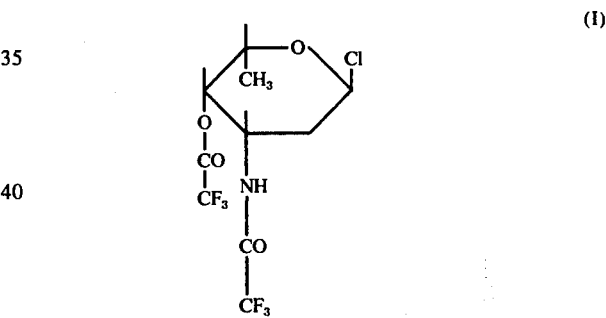

(I)

with a hydrogen chloride acceptor, such as, mercuric oxide, a silver oxide, or a mercury or silver salt, such as $Hg(CN)_2$ or $Ag_2CO_3$ or inorganic bases such as potassium hydroxide, sodium hydroxide, alkali metal carbonates or organic bases such as substituted amines, in an organic solvent such as, for example, benzene, toluene, nitromethane, dioxane or the like, or mixtures thereof, either at room temperature or at a temperature up to the boiling point of the solvent or solvent mixture.

It is of course to be understood that the 4'-epimer and the 6'-hydroxy derivative of structure (II), also appropriately protected by trifluoroacetyl groups, may also be used as the glycal. Likewise, it is to be understood that protective groups other than the trifluoroacetyl group may also be advantageously employed. These protective groups derive from aliphatic or aromatic acids with electron attracting groups such as dichloroacetyl group, trichloroacetyl group or p-nitrobenzoyl, p-chlorobenzoyl, p-bromobenzoyl groups.

According to a further aspect of the invention, the novel reactive protected 1,2-unsaturated pyranoid sugar of the formula (II) is utilized in a process for the preparation of anthracyclinone glycoside antibiotics of the formula (VIII). According to this latter process, an anthracyclinone compound of the formula (III):

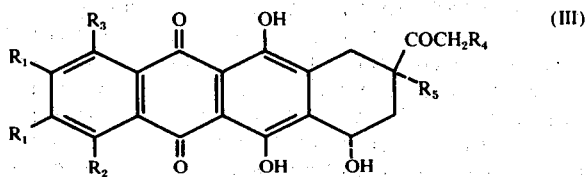

wherein when $R_1$ is hydrogen, $R_2$ and $R_3$ are each independelty hydrogen, methyl, methoxy, chloro or bromo; and when $R_2$ and $R_3$ are hydrogen, $R_1$ is methyl, chloro or bromo and $R_4$ and $R_5$ are each independently hydrogen or hydroxy or a dioxolanyl derivative thereof having the formula (VI):

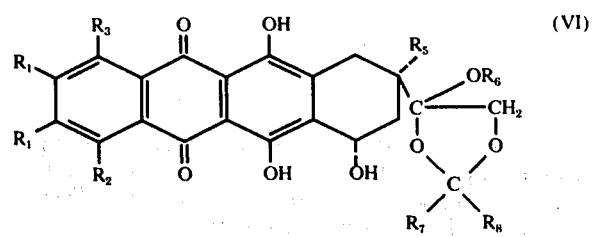

wherein $R_1$, $R_2$, $R_3$, $R_4$ and $R_5$ are as defined above, and $R_6$, $R_7$ and $R_8$ are independently selected from the group consisting of hydrogen and $C_1$–$C_4$ alkyl; or $R_7$ and $R_8$, together with the carbon atom to which they are bound may form a saturated or unsaturated ring of 3–8 carbon atoms is subjected to an acid catalyzed addition reaction with the glycal of formula (II) to obtain, after removal of the protecting groups, the glycoside antibiotics of the formula (VIII).

In the case of the preparation of daunomycin, the anthracyclinone compound of formula (III) wherein $R_1=R_3=R_4$=hydrogen, $R_2$=methoxy and $R_5$=hydroxy is reacted with compound (II), In the case of the preparation of adriamycin, the dioxolanyl derivative of the formula (VIA), i.e., compound (VI) wherein $R_1=R_3$=hydrogen, $R_2$=methoxy, $R_5$=hydroxy and $R_6=R_7=R_8$=methyl is reacted with compound (II).

The acid catalyst used in the addition reaction may be a sulfonic acid, e.g., p-toluene sulfonic acid or methane sulfonic acid.

The addition reaction may advantageously be performed in a suitable solvent such as benzene, toluene, or nitromethane. When the addition reaction is completed, the mixture is neutralized by stirring with solid sodium bicarbonate followed by filtration, and then evaporated in vacuo to a residue.

The resulting residue is then subjected to suitable hydrolysis to remove the protecting groups. In the case of the preparation of daunomycin, an alkaline hydrolysis is employed to remove the protecting groups. In the case of the preparation of adriamycin, an alkaline hydrolysis, followed by an acid hydrolysis are employed.

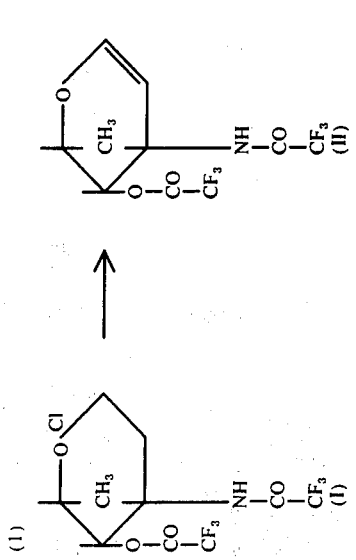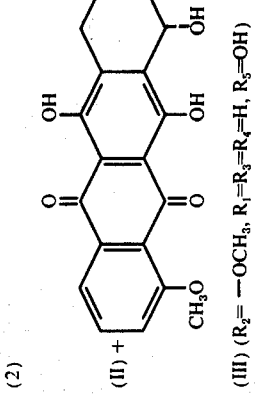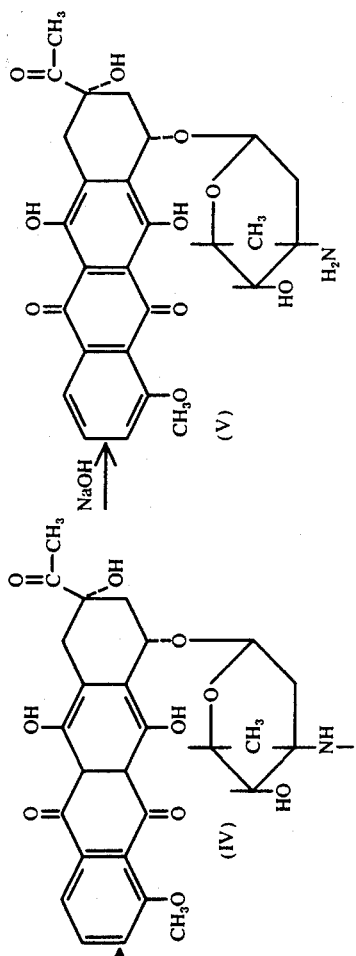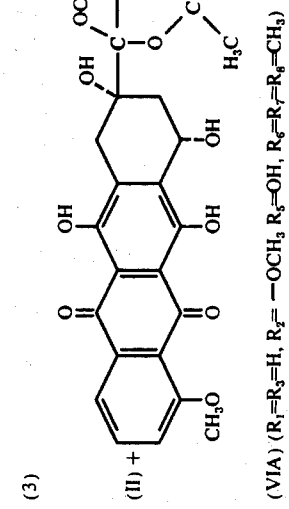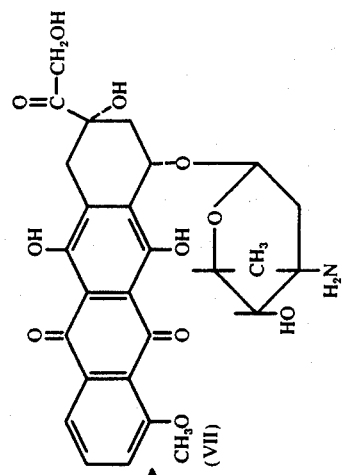

DESCRIPTION OF THE PREFERRED EMBODIMENTS

In the following examples which further illustrate the invention, all parts given are by weight unless otherwise indicated.

EXAMPLE 1

Preparation of 1,2,3,6-tetradeoxy-3-trifluoroacetamido-4-trifluoroacetoxy-L-lyxo-hex-1-enopyranose (II) from 1-chloro-2,3,6-trideoxy-3-trifluoroacetamido-4-trifluoroacetoxy-alpha-L-lyxohexopyranose (I)

To a solution of 800 mg of 1-chloro-2,36-trideoxy-3-trifluoroacetamido-4-trifluoroacetoxy-alpha-L-lyxohexopyranose (I)* in 25 ml of a 4:1 (by volume) mixture of benzene and dioxane there were added 500 mg of $Hg(CN)_2$. The resulting suspension was heated under reflux for 3 ½ hours. After cooling, the reaction mixture was filtered to give a clear solution, which was then evaporated to a residue. The residue was extracted with benzene and, upon evaporatiion of the benzene solution, there were obtained 650 mg of 1,2,3,6-tetradeoxy-3-trifluoroacetamido-4-trifluoroacetoxy-L-lyxo-hex-1-enopyranose )II) in crystalline form melting at 73°–74° C.

*Compound (I) was prepared according to the procedures described in the copending application of Arcamone, DiMarco, and Penco, and in particular, in Examples 1 and 2 thereof, entitled "Daunomycins, Process for Their Preparation and Uses Thereof", filed on Mar. 19, 1975 and owned by the unrecorded assignee hereof. The contents of said application are expressly incorporated herein by reference.

Compound (II) was characterized by NMR and mass spectroscopy, as follows:

| NMR ($CDCl_3$): | 1.28 δ | (d, J=6.5Hz, 3H, $CH_3$) |
|---|---|---|
| | 4.25 δ | (dq, J=6.5Hz and J<1Hz, 1H, $C_{(5)}H$) |
| | 4.51 δ | (dt, J=6.0Hz and J=2.0Hz, 1H, $C_{(2)}H$) |
| | 4.7–5.2 δ | (broad m, 1H, $C_{(3)}H$) |
| | 5.2–5.6 δ | (m, 1H, $C_{(4)}H$) |
| | 6.20 δ | (broad, s, 1H, NH) |
| | 6.50 δ | (dd, J=6.5Hz and J=2.0Hz, 1H, $C_{(1)}H$) |
| MS (DIS): | m/c 322 (M + 1) | |
| | m/c 207 (M − $CF_3COOH$) | |
| | m/c 192 (M − $CF_3COOH-CH_3$) | |
| | m/e 16S (HO=$\overset{+}{C}$H—$\overset{1}{C}$H—$\overset{2}{C}$H—NH—$\overset{3}{C}$OCF$_3$) | |
| | m/e 154 ($CF_3$—CO—O—$\overset{4}{C}$H=$\overset{3}{C}$H—$\overset{+}{N}$H—) | |

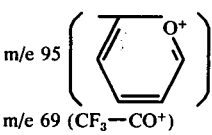

m/e 95 m/e 69 ($CF_3$—$CO^+$)

EXAMPLE 2

Alternate Preparation of Compound (II)

A 100 mg suspension of $Hg(CN)_2$ in 40 ml of a 1:1 (by volume) mixture of anhydrous nitromethane and benzene was heated to the boiling point and 25 ml of the solvent were distilled off. To the resulting suspension, 100 mg of Compound (I) were added and the mixture was heated at reflux temperature for 2 ½ hour. The mixture was evaporated to a residue under vacuum and the residue was thereafter extracted with anhydrous benzene. On evaporation of the benzene extract, Compound (II) was obtained in 85% yield (m.p. 73°–74° C).

EXAMPLE 3

Alternate Preparation of Compound (II)

100 mg of Compound (I) were added to a suspension of 80 mg of $Ag_2CO_3$ in 3 ml of nitromethane. The resulting mixture was stirred overnight at room temperature and was then filtered. After evaporation of the filtrate, substantially pure Compound (II) was obtained in 80% yield (m.p. 72°–73° C).

EXAMPLE 4

Preparation of Daunnomycin (V)

200 mg of Daunomycinone (III) were dissolved in 100 ml of anhydrous benzene and treated with 320 mg of compound (II) in 5 ml of anhydrous benzene and 13 mg of p-toluene salfonic acid. The mixture was heated at 50° C for 4 hour. After cooling and neutralization with pyridine, the solution was evaporated to a residue, which was dissolved in 50 ml of anhydrous methanol and heated at 55° C for 1 hour. The solvent was removed by evaporation under vacuum and the residue was dissolved in chloroform. The chloroform solution was washed with water, dried over sodium sulfate, concentrated to a small volume, and placed on a silica gel column which was eluted with chloroform containing increasing amounts of ethyl acetate from zero to a final concentration of 20% of ethyl acetate. The yield, after crystallizing from tetrahydrofuran and hexane was 145 mg (50%) of N-trifluoroacetyl daunomycin (IV), m.p. 170°–171° C, $[alpha]_D 23° = + 235°$ (c 0.1 $CHCl_3$). The NMR data were as follows:

NMR ($CDCl_3$):
1.32 δ: [d, J=6.54, $CH_3$—C(H)]
2.40 δ: (s, $CH_3CO$)
4.02 δ: (s, $CH_3O$)
5.17 δ; (broad s, $c_{(7)}H$)
12.85 and 13.60 δ: [two s, chelated OH at $C_{(6)}$ and $C_{(11)}$]

100 mg of the N-trifluoroacetyl daunomycin were dissolved in 20 ml of 0.1N aqueous sodium hydroxide. After 1 hour at room temperature, the solution was treated with 0.5N aqueous hydrogen chloride to bring the pH to 8.5, and was then extracted with chloroform. The chloroform extract, after drying over sodium sulfate, was concentrated to a small volume and upon addition of one equivalent of IN methanolic hydrogen chloride, Daunomycin (V) (as the hydrochloride) was obtained in crystalline form. Yield: 70 mg; m.p. 188°–189° C (decomposed);
$[alpha]_D 23° = + 240°$ (c 0.1 $CH_3OH$).

EXAMPLE 5

Preparation of Adriamycin (VII)

550 mg of 9-desacetyl-9-(2',2'-dimethyl-4'-methoxy-4'-dioxolanyl)-daunomycinone, Compound (VIA)* were dissolved in 100 ml of anhydrous benzene and treated with 650 mg of Compound (II) in 10 ml of anhydrous benzene and 26 mg of p-toluene sulfonic acid. The mixture was heated at 30° C for 3 hours, then neutralized with pyridine and evaporated to a residue. The residue was dissolved in 10 ml of acetone and then treated with 50 ml of 0.1N aqueous sodium hydroxide. After 30 minutes at room temperature the pH of the solution was adjusted to 8.4 with aqueous hydrogen chloride, and the solution was then repeatedly extracted with chloroform. The combined chloroform extracts were dried over anhydrous sodium sulfate, filtered and evaporated under vacuum. The residue was taken up in 0.1N aqueous hydrogen chloride and left at room temperature for 36 hours. The acid solution was washed by extraction with chloroform, to remove traces of the aglycone, then brought to a pH of 8.6, under stirring and in the presence of 50 ml of chloroform, by slowly adding 0.1N aqueous sodium hydroxide. The organic phase was then separated, dried over anhydrous sodium sulfate, and concentrated to 10 ml. Adriamycin (VII), as the hydrochloride, was crystallized by addition of one equivalent of 1N methanolic hydrogen chloride. The yield was 420 mg; m.p. 204°–205° C, $[alpha]_D 23° = + 230°$ (c 0.05 $CH_3OH$).

*Compound (VIA) was prepared according to the procedures described in the copending application of arcamone, DiMarco and Penco, and in particular, Example 1 thereof, entitled "Adriamycins, Process for Their Preparation and Uses Thereof", filed on Mar. 19, 1975 and owned by the unrecorded assignee hereof. The contents of said application are expressly incorporated herein by reference.

The same results may readily be achieved when, in lieu of Compound (VIA), another suitable protected reactive derivative of adriamycinone is used.

Variations can, of course, be made without departing from the spirit and scope of the invention.

Having thus described the invention, what is desired to be secured by Letters Patent and hereby claimed is.

What is claimed is:

1. 1,2,3,6-Tetradeoxy-3-trifluoroacctamido-4-trifluoroacetoxy-L-lyxo-hex-1-enopyranose.

* * * * *

UNITED STATES PATENT OFFICE
CERTIFICATE OF CORRECTION

Patent No. 4,020,270    Dated 4/26/77

Inventor(s) Federico Arcamone and Giuseppe Cassinelli

It is certified that error appears in the above-identified patent and that said Letters Patent are hereby corrected as shown below:

Title page, formula (VI) in the Abstract:

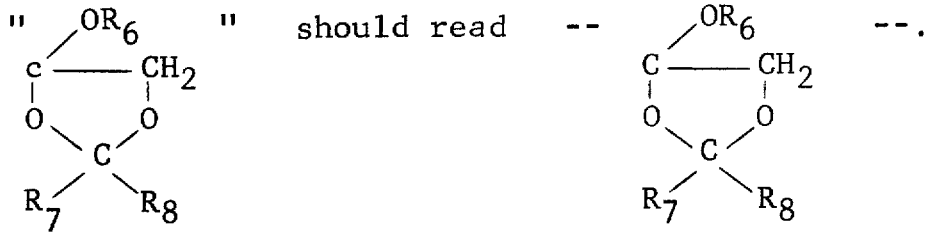

Column 1, line 36: "Glyceside" should read -- Glycoside --.

Column 3, lines 15-16: "independelty" should read -- independently --.

Columns 5-6, top of the page: should read -- The overall sequence may be illustrated as follows: --; formula (I):

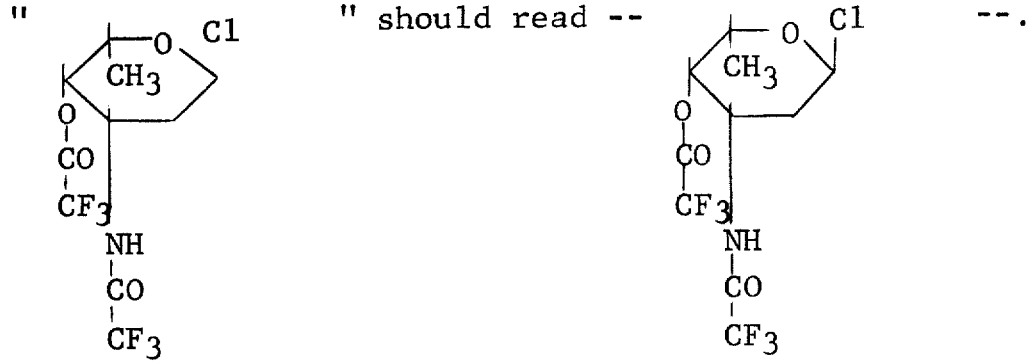

UNITED STATES PATENT OFFICE
CERTIFICATE OF CORRECTION

Patent No. 4,020,270    Dated 4/26/77

Inventor(s) Federico Arcamone and Giuseppe Cassinelli

It is certified that error appears in the above-identified patent and that said Letters Patent are hereby corrected as shown below:

Column 7, line 15: "1-chloro-2,36-trideoxy-3-" should read -- 1-chloro-2,3,6-trideoxy-3- --; lines 43-45: "m/c" should read -- m/e --; line 46: "m/e 16S" should read -- m/e 168 --; line 64: "2 1/2 hour." should read -- 2 1/2 hours. --.

Column 8, line 13: "Preparation of Daunnomycin(V)" should read -- Preparation of Daunomycin (V) --; line 17: "salfonic" should read -- sulfonic --; line 34: "[d, J=6.54, $CH_3$-C(H)]" should read -- [d, J=6.5H, $CH_3$-C(H)] --; line 37: "(broad s, $c_{(7)}$H)" should read -- (broad s, $C_{(7)}$H) --.

Column 10, line 2: "arcamone," should read -- Arcamone, --.

Signed and Sealed this

Thirteenth Day of June 1978

[SEAL]

Attest:

RUTH C. MASON
*Attesting Officer*

DONALD W. BANNER
*Commissioner of Patents and Trademarks*